United States Patent [19]

Prekel et al.

[11] Patent Number: 5,760,400

[45] Date of Patent: Jun. 2, 1998

[54] METHOD AND A DEVICE FOR PHOTOTHERMALLY TESTING WORKPIECES

[75] Inventors: Helmut Prekel, Lindau; Horst Adams, Nonnenhorn, both of Germany

[73] Assignee: Wagner International AG, Alstatten, Switzerland

[21] Appl. No.: 675,410

[22] Filed: Jul. 2, 1996

[30] Foreign Application Priority Data

Feb. 21, 1996 [DE] Germany ................. 196 06 453.8

[51] Int. Cl.[6] ........................... G01N 21/71; G01N 21/01
[52] U.S. Cl. ........................ 250/341.6; 250/341.7; 250/341.8
[58] Field of Search ................... 250/341.6, 341.7, 250/341.8, 358.1, 359.1, 360.1; 378/63, 206

[56] References Cited

U.S. PATENT DOCUMENTS 2,659,824  11/1953  Burnham ..................... 378/206

FOREIGN PATENT DOCUMENTS

| 0 279 347 | 10/1988 | European Pat. Off. . |
| 0 609 193 | 1/1994 | European Pat. Off. . |
| 3631652 | 9/1986 | Germany . |
| 43 43 076 | 6/1995 | Germany . |
| 2 212 040 | 7/1989 | United Kingdom ........... 378/206 |

OTHER PUBLICATIONS

"Thermal Wave Interferometry", C.A. Bennett, Jr. and R.R. Patty, Applied Optics, vol. 21 No. 1, Jan., 1982, pp. 49 to 54.

Primary Examiner—Constantine Hannaher
Attorney, Agent, or Firm—Hill & Simpson

[57] ABSTRACT

A method for photothermally testing workpieces, which includes the steps of directing an electromagnetic excitation beam to a desired measuring point on the workpiece surface, detecting and evaluating the heat in the form of thermal radiation which is generated by the excitation beam at the measuring point with the aid of a measuring head; directing two visible locating beams to the workpiece surface, the two locating beams intersecting at a point of intersection; and correcting the relative position between the workpiece and the measuring head so that the point of intersection and the desired measuring point coincide on the workpiece surface.

18 Claims, 1 Drawing Sheet

METHOD AND A DEVICE FOR PHOTOTHERMALLY TESTING WORKPIECES

BACKGROUND OF THE INVENTION

The present invention relates to the testing of materials. More specifically, the present invention relates to a method of photothermally testing workpieces.

Photothermal, contactless and non destructive testing of materials by thermally excitating surfaces with the help of intensity modulated radiation and evaluating the variation in time of the thermal radiation produced by said surfaces is known. The fundamental principle, also known as photothermal radiometry, is based on the generation of thermal waves in a device under test which spread out in a manner characteristic for the nature of the material used for the device under test and which, similar to ultrasound waves, are diffused and reflected at thermal non-uniformities, such as layer boundaries, delaminations, cracks, pores etc. The reflected or diffused portions of the thermal waves interfere with the original or excitation wave and form, partly after multiple reflections and/or dispersions, a summation vector of the thermal wave. Said vector comprises a vector amount and a vector phase as measuring information about a workpiece to be tested wherein the vector amount is not very useful due to its substantial dependency of external factors such as the measuring distance and the angle between the excitation beam and the workpiece which in industrial applications often cannot be adjusted precisely. The phase is essentially independent of said parameters and even of the power of the intensity modulated excitation beam so that it can be evaluated reliably. Based on the phase offset between the infrared thermal radiation emitted from the workpiece and the excitation beam directed to the workpiece the characteristics of a workpiece, in particular the thickness of the workpiece surface, can be determined.

It is advantageous to choose the excitation beam so that its wavelength(s) lie(s) outside of the sensitivity range of the infrared detector. Thus, it is avoided, that the dispersed and/or reflected excitation radiation produces an error signal in the detector.

Photothermal radiometry is particularly useful for workpieces which are thermally thin such as surface coatings and protection layers on workpieces, because in this case interferences of thermal waves are most noticeable. Further theoretical aspects of photothermal radiometry can be found in C. A. Bennet, Jr. and R. R. Patty, "Thermal Wave Interferometry: A Potential Application of the Photoacoustic Effect", Applied Optics, Volume 21, No. 1, Jan. 1, 1982, pages 49 to 54.

A device for non-destructive testing of materials is known from the European patent application EP-A-0 609 193. In this reference a modulated laser beam or a continuous laser beam, which is modulated (periodically interrupted) by a mechanical interrupter, is directed to a test surface so that said surface is periodically heated, the heating being detected by an infrared detector, converted and supplied to a computer for evaluation in order to determine the porosity of friction linings.

Another set-up for photothermally testing materials and measuring the thickness of a coating is taught in the German patent application DE-A-36 31 652. FIG. 1 of this reference shows a heat emitter, followed by a modulator so that intensity modulated radiation is transmitted to a test surface, in this case via fibers.

The photothermal measuring technique is particularly useful for measuring the thickness of a layer of powder coating on a workpiece which has not yet been burnt-in, i.e. before the workpiece is transferred into the stove furnace. A measurement of this kind may be performed using an infrared laser, e.g. a $CO_2$ infrared laser.

A further device for photothermally testing workpieces is known from the German patent application, DE-A-43 43 076, wherein an (invisible) excitation beam and an (invisible) measuring beam are collinearly aligned.

A problem with the prior art methods and devices for photothermally testing workpieces is that both the exciting (laser) beam as well as the (infrared) heat radiation emitted from the powder on the workpiece, used as measuring signal, are within the infrared spectral range and are, therefore, not visible to the human eye. Therefore, a user cannot determine where exactly the excitation beam meets the workpiece surface. However, in many cases it is desirable to exactly position the measuring point on the workpiece.

An object of the present invention is to provide a method and a device for photothermally testing workpieces, where it is possible to exactly monitor the location of a desired measuring point on a workpiece.

SUMMARY OF THE INVENTION

According to a first aspect of the present invention this object is solved by a method of photothermally testing workpieces, comprising the steps of: directing an electromagnetic excitation beam to a desired measuring point on the workpiece surface; detecting and evaluating the heat in the form of thermal radiation which is generated by the excitation beam at the measuring point with the aid of measuring means; directing two visible locating beams to the workpiece surface, the two locating beams intersecting at a point of intersection; and correcting the relative position between the workpiece and the measuring means so that the point of intersection and the desired measuring point coincide on the workpiece surface.

According to a second aspect of the present invention this object is solved by a device for photothermally testing workpieces, comprising: excitation source means for outputting an electromagnetic excitation beam; optical means for directing the excitation beam to a measuring point on the workpiece surface; measuring means for detecting thermal radiation emitted from the workpiece; locating means for producing two visible locating beams, which intersect at a point of intersection; optical deflecting means for directing the locating beams to a workpiece surface; and displacement means for correcting the distance between the measuring means and the workpiece so that the point of intersection coincides with the measuring point on the workpiece surface.

With the method and the device according to the present invention it is possible to visualize a desired measuring point on the workpiece. The locating beams are directed to the workpiece surface so that when the workpiece is in front of or behind a desired position, as seen from the measuring device, two light points are visible on the workpiece surface whereas in the desired position one light point, namely the intersecting point of the two locating beams at the desired measuring point on the workpiece surface is visible. In this manner a very simple adjustment of the distance between the workpiece and the measuring device as well as an optical control are provided to verify that the measuring point lies exactly at the desired position of the workpiece surface.

This is advantageous e.g. for irregular workpieces where the measurement at one position or at a plurality of precisely defined positions on the workpiece surface shall be made.

By adjusting the distance between the workpiece and the measuring means the thermal radiation produced by the workpiece is utilized optimally. Adjusting and maintaining the right distance of the workpiece to the measuring device is important because the heat radiation emitted from the workpiece (or the coating, such as the powder, respectively) will usually be mapped on the detector by means of a focusing optic which is located at a short distance in front of the detector. The focusing optic is inserted because the actual detector crystal (InSb; indium antimony) only has a size in the millimeter range; on the other hand, the radiation is to be detected from a larger dihedral angle area to increase the intensity of the measuring signal.

For an optimum operation of the focusing optic it is desirable that the detector crystal is located exactly at one focal point of the focusing optic (which can be ensured by constructional measures) and that the workpiece surface is positioned exactly at the other focal point. With the present invention this kind of positioning can be achieved.

The exact knowledge of the distance between the workpiece and the measuring device has a further advantage. As disclosed in the Background of the Invention, the measuring information about the device under test comprises a vector amount and a vector phase wherein the vector amount is among other things dependent on the measuring distance. However, with the present invention the distance of the measuring point to the detector can be adjusted to a desired value and, therefore, the information about this distance may also be used, when evaluating the thermal radiation detected by the detector.

According to a preferred embodiment of the present invention the locating beams define an acute angle (<90°) and are directed to the workpiece surface symmetrically to the normal line of the workpiece. The workpiece normal line or the axis of symmetry, respectively, preferably coincide with the longitudinal axis of a detector of the measuring device to ensure that the measuring point is located precisely opposite the detector means. The intersecting point of the locating beams and, accordingly, the desired measuring point according to the present invention preferably lie at the focal point of a focusing optic placed in front of the detector.

It is especially advantageous if the locating beams are produced by one source only, in which one single visible laser beam is separated into two sub-beams. This helps to keep the number of costly components for the testing system as low as possible.

In the past, when photothermally measuring the thickness of a layer, prior art techniques always applied the excitation beam coaxially to the detector beam (heat radiation) emitted by the workpiece, i.e. in a direction orthogonal to the workpiece, without visualizing the measuring position on the workpiece. Control of the distance between the detector and the workpiece was not possible. According to a preferred embodiment of the present invention, however, this principle of collinearity is given up and the excitation beam is directed to the workpiece surface with an acute angle to the normal line of the workpiece. When, in this case, one of the locating beams is superimposed onto the excitation beam, the same components of an optical deflecting system for directing the excitation beam can also be used for said one locating beam. Thus, component redundancies can be avoided. The second locating beam is then directed symmetrically to the first locating beam, as mentioned above.

The excitation beam usually is an intensity modulated invisible laser beam in the infrared range.

An especially compact system may be achieved when the functions of producing and directing the locating beams and of detecting the heat radiation are integrated in one measuring head; correcting the relative position between the workpiece and the measuring device can then be performed by simply moving the measuring head and accordingly the measuring device as a whole.

The device for realizing the method of the present invention preferably comprises at least one locating laser for generating a visible laser beam wherein the presently preferred lasers are diode lasers or He/Ne lasers.

Usually, the excitation source comprises one excitation laser for generating an invisible laser beam in the infrared range the intensity of which is modulated by the optical means. Preferably, the excitation laser is a $CO_2$ laser.

In a particularly advantageous embodiment of the present invention an optical deflecting system directs the locating beams symmetrically to a normal line of the workpiece to the workpiece surface wherein, for the reasons mentioned above, one of the locating beams is superimposed on the excitation beam. Further, the optical deflecting system may comprise a beam separator for separating a visible laser beam into two sub-beams so that only one laser has to be provided as a source for the locating beams.

In one embodiment of the invention a single visible laser beam is separated by an optical deflecting system comprising two parallel 45° mirrors one of which is 50% transparent.

When the locating means is integrated in the measuring means, the translation means can include an actuator means for correcting the position of the measuring means relative to the workpiece.

The device and the method according to the present invention are particularly suitable for measuring thicknesses of a layer of a surface coating.

The above and other objects, advantages, aspects and features of the present invention will be more fully understood and appreciated by those skilled in the art upon consideration of the following detailed description of a preferred embodiment, presented in conjunction with the accompanying drawings.

DETAILED DESCRIPTION OF THE PREFERRED EMBODIMENTS

Figure 1:
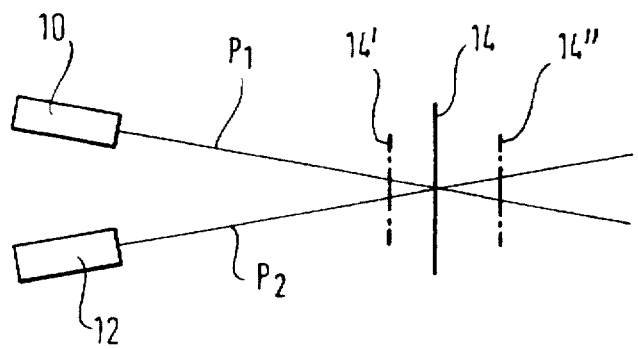
FIG. 1 shows a schematic diagram of the "two point principle" according to the present invention.

FIG. 1 very schematically shows one aspect of the present invention in a basic diagram.

In FIG. 1 two light sources 10, 12 generate two locating beams $P_1$ and $P_2$, respectively, which are directed to a workpiece 14 and which intersect at the desired measuring point so that with the method and the device according to the present invention for testing workpieces and, in particular, for measuring the thickness of a surface coating of the workpiece, the measuring point can be positioned exactly at the focal point of the detector means. If, however, the workpiece 14 is positioned in front of (14') or behind (14") the desired position two light points are visible on the workpiece surface, whereas in the desired position (14) only one point is visible. Under consideration of this information adjustment of the position of the workpiece or the workpiece surface, respectively, is possible, so that the measuring point and the focal point of the detector device coincide.

The locating beams $P_1$, $P_2$ preferably are visible laser beams wherein the presently preferred embodiment of the invention uses a diode laser or an He/Ne laser as a light source. The locating beams define an acute angle, e.g. in the range from 100 to 450, and further, the beams are symmetrically aligned to a normal line of the workpiece. With the above dimensions a good resolution of the light points projected onto the workpiece surface can be achieved.

In an alternative embodiment of the invention the two visible locating beams $P_1$, $P_2$ are generated with different colors (e.g. red and green). This produces the additional information whether the workpiece is located in front of or behind the intersection of the locating beams, i.e. in front of or behind its desired position, which can be derived from the order of the colored locating beam points depicted on the workpiece surface. A further possibility to obtain this kind of information is to periodically interrupt one of the locating beams to produce a blinking beam. Generally speaking, by designing the two locating beams differently it is possible to visualize on the workpiece surface whether the workpiece 14 is in front of or behind its desired position.

Figure 2:
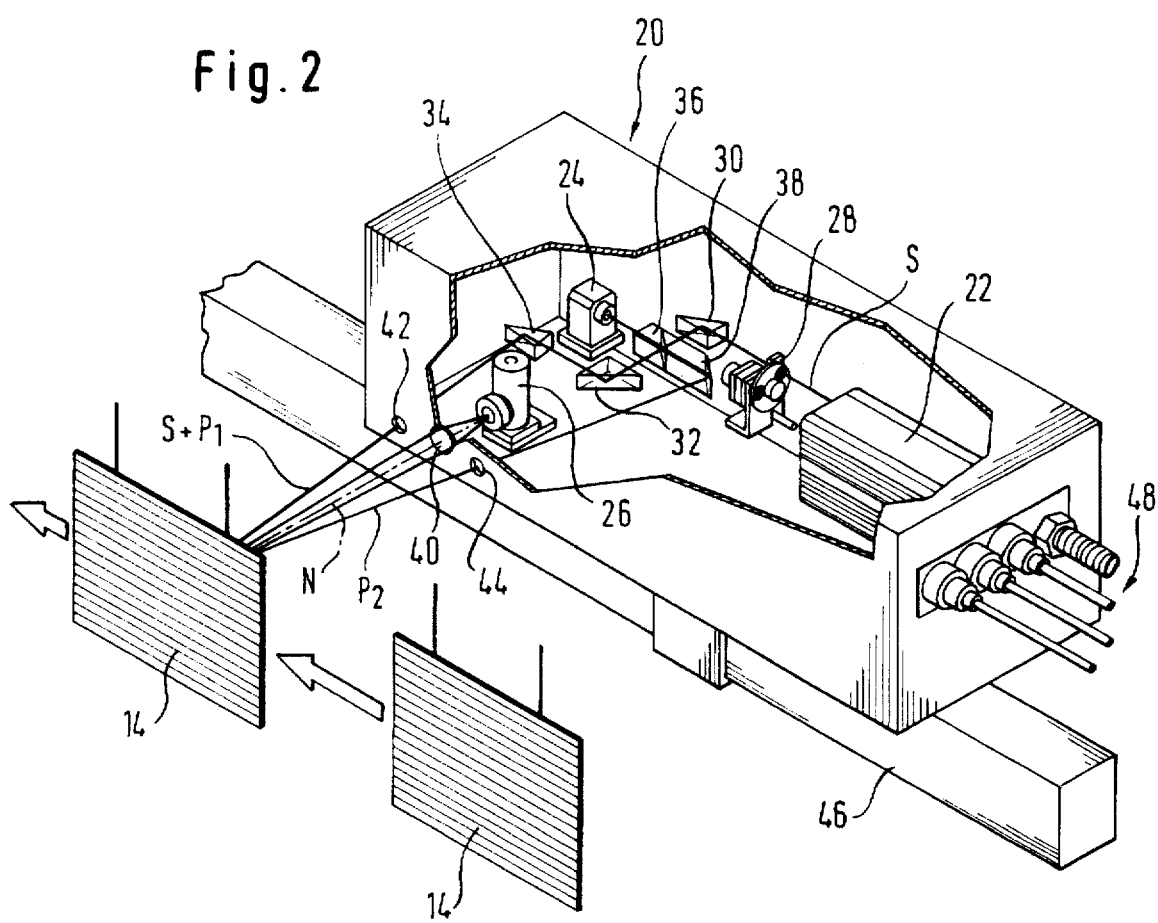
FIG. 2 shows a schematic perspective view of one embodiment of the present invention.

FIG. 2 shows a device for photothermally measuring the thickness of a layer or a coating according to the present invention with parts of the device broken away.

The measuring or testing device shown in FIG. 2 comprises a measuring head 20 including an excitation source 22, a locating light source 24 and a detector means 26. Further, a chopper means 28 and an optical deflecting system 30, 32, 34, 36, 38 are provided in the measuring head. A focusing optic 40 is provided in front of the detector means 26. Further, the measuring head has two openings 42, 44.

The measuring head 20 is movably supported on a guide rail 46 and, in the shown embodiment of the invention, the distance between the measuring head and the workpiece 14 is about one meter. An actuator means for moving the measuring head 20 is not shown in the figure. An actuator means would preferably be provided on the rail 46. The measuring head 20 comprises terminals 48 for supplying power and control signals to the measuring head and for transmitting measuring signals from the measuring head.

Now the operation of the device shown in FIG. 2 will be described. The workpieces 14 are transported past the measuring head 20 in the direction of the arrow with a distance of about one meter to the measuring head. Said measuring head sends, on the right-hand side of the drawing, an excitation beam S from an excitation source 22 through a chopper 28. In the shown embodiment the excitation beam S is an invisible $CO_2$ laser beam which is modulated by the chopper or "fan" having dark barrier areas and transparent pass areas. A periodically interrupted "heating beam" is produced which is directed by means of a deflecting system comprising three prisms 30, 32, 34; the heating beam is directed through the opening 42 in the measuring head 20 and, with an acute angle, onto the surface of the workpiece. Heat generated by locally heating the workpiece is emitted in a direction orthogonal to the workpiece with the highest intensity and enters a vertical cylindrical detector 26 of the measuring head 20. The detector 26 measures the intensity of the heat radiation; and therefrom the thickness of a layer of a workpiece coating is derived in a manner known in the art. A focusing optic 40 is positioned between the workpiece 14 and the detector 26, the focusing optic bundling the thermal radiation emitted from the workpiece 14 and focusing said thermal radiation onto a very small detector crystal in the detector means 26.

In order to arrive at an optimum evaluation of the thermal radiation emitted from the workpiece 14 the excitation beam S must meet the workpiece 14 in or very close to a precisely localized measuring point having a defined distance to the detector means 26. According to the present invention, the precise adjustment of the relative position between the workpiece 14 at the measuring head 20 is achieved by means of a locating means and a displacement means.

In prior art devices for photothermally measuring coating thicknesses the measuring point, i.e. the point where the excitation beam hits the workpiece surface, has been invisible because usually an invisible heating beam, e.g. from a $CO_2$ laser, had been used. Therefore, it has been difficult to locate and adjust the desired measuring point, and, in particular, the desired measuring distance between the workpiece 14 and the measuring head 20.

In the device for measuring a coating thickness according to the invention, as shown in FIG. 2, a light source 24, preferably a diode laser or a helium/neon laser (He/Ne laser), is provided, the visible output beam of which is separated into two visible locating beams $P_1$, $P_2$ by means of an optical deflecting system 36, 38. To this end, two parallel 45° mirrors are disposed facing the light output of the laser 24, a first one 36 of the mirrors being 50% transparent and the second one 38 fully reflecting the "remaining" beam which passed the first mirror 36. Further, the first 45° mirror 36 can be passed by the IR-beam of the excitation laser from back to front.

The deflecting system composed of the two 45° mirrors 36, 38 is designed so that the first sub-beam, corresponding to the first locating beam $P_1$, is superimposed onto the modulated excitation beam S and is directed to the workpiece surface combined with the excitation beam at an acute angle. A second sub-beam, corresponding to the locating beam $P_2$, is directed to the workpiece mirror-invertedly, a normal line on the workpiece forming an axis of symmetry. This workpiece normal line or axis of symmetric is collinear to the axis of detection N of the detector 26.

If the distance between the measuring head 20 and the workpiece 14 is too short or too long, two light points appear on the workpiece. By adjusting the position of the measuring head 20 relative to the workpiece 14 via the guide rail 26 and the actuator means (not shown) the light points of the locating beams $P_1$ and $P_2$ can be made to coincide so that also the "meeting point" of the invisible excitation beam S is at this intersection of the locating beams and the desired measuring point can be visualized and verified on the workpiece.

Even when visible light would be suitable for use as an excitation beam, the projection of one single excitation beam on the workpiece surface collinearly with the heat radiation from the workpiece, as in the prior art, the exact spatial position of the measuring point on the workpiece could not be controlled. In the method and the device according to the present invention, by directing said two locating beams $P_1$, and $P_2$ to the workpiece so that a desired measuring point is at the intersection of the two locating beams and by correcting the distance between the workpiece and the measuring head, the desired measuring point can be visualized precisely on the workpiece and adjusted. If, as mentioned above, also visible light would be suitable as an excitation beam, in an alternative embodiment of the invention the excitation beam itself could be divided into two sub-beams which are directed to the workpiece in a way similar to the two locating beams $P_1$, $P_2$, above, in order to both generate local heating of the workpiece and to visualize the "meeting point", i.e. the desired measuring point. The excitation beam S would then have the double function of thermally exciting the workpiece and visualizing the measuring point.

Of course, the present invention is not restricted to the details of the device for photothermally measuring the thickness of a workpiece coating described above. If e.g. a measuring system concurrently directs an excitation beam to two or more different test points on a workpiece surface it would be appropriate to provide either a plurality of light sources or additional beam separators in order to generate a sufficient number of locating beams or sub-beams (two for each excitation beam directed to a measuring point).

The features defined in the above specification, the drawings and the claims may be essential for realizing the present invention either alone or in any combination thereof. To those skilled in the art many changes and modifications will be readily apparent from consideration of the foregoing description of a preferred embodiment without departure from the spirit and scope of the present invention.

What is claimed is:

1. A method for photothermally testing a workpiece having a surface comprising the steps of:

directing an electromagnetic excitation beam to a desired measuring point on the workpiece surface;

detecting and evaluating thermal radiation on said workpiece surface generated at said desired measuring point by said excitation beam and reflected from said measuring point by thermal radiation measuring means;

directing at least two visible locating beams to the workpiece surface, said locating beams intersecting at a point of intersection; and correcting the relative position between the workpiece and the thermal radiation measuring means such that the point of intersection of said visible location beams and the desired measuring point coincide on the workpiece surface.

2. The method of claim 1, wherein the visible locating beams define an acute angle.

3. The method of claim 1, wherein the visible locating beams are directed to the workpiece surface symmetrically to an axis which is perpendicular to said workpiece surface.

4. The method of claim 1, wherein the visible locating beams are generated by separating a visible laser beam into two sub-beams.

5. The method of claim 1, wherein one of said locating beams is superimposed on the excitation beam.

6. The method of claim 1, wherein the excitation beam is an intensity modulated invisible laser beam in the infrared range.

7. The method of claim 1, wherein the locating beams are emitted by the thermal radiation measuring means and the relative position between the workpiece and the measuring means is corrected by moving said measuring means.

8. A device for photothermally testing a workpiece having a surface comprising: excitation source means for outputting an electromagnetic excitation beam;

optical means for directing the excitation beam to a measuring point on the workpiece surface;

thermal radiation measuring means for detecting thermal radiation emitted from the measuring point on the workpiece surface;

locating means for producing two visible locating beams, which intersect at a point of intersection;

optical deflecting means for directing the locating beams to a workpiece surface; and displacement means for correcting the distance between the measuring means and the workpiece so that the point of intersection coincides with the measuring point on the workpiece surface.

9. The device of claim 8, wherein the locating means comprises at least one locating laser for generating a visible laser beam.

10. The device of claim 9, wherein the locating laser is a diode laser or a He/Ne laser.

11. The device of claim 8, wherein said excitation source means comprises an excitation laser for generating an invisible laser beam in the infrared range and modulation means for modulating the intensity of said laser beam.

12. The device of claim 11, wherein said excitation laser is a $CO_2$ laser.

13. The device of claim 8, wherein said locating means comprises an optical deflecting system for directing said locating beams symmetrically to a normal line of the workpiece.

14. The device of claim 13, wherein said optical deflecting system superimposes one of said locating beams and said excitation beam.

15. The device of claim 13, wherein said optical deflecting system comprises a beam splitter for separating a visible laser beam into two sub-beams.

16. The device of claim 13, wherein said optical deflecting system comprises two parallel 45° mirrors, one of the mirrors being 50% transparent.

17. The device of claim 8, wherein said locating means is integrated into said measuring means and, an actuator means is provided for correcting the position of said measuring means relative to the workpiece.

18. A method of measuring the thickness of a workpiece coating, the workpiece coating including a surface, comprising the steps of:

directing an electromagnetic excitation beam to a desired measuring point on the surface of the workpiece coating;

detecting and evaluating the thermal radiation which is generated by the excitation beam at the measuring point by means of thermal radiation measuring means;

directing at least two visible locating beams to the workpiece coating surface, the two locating beams intersecting at a point of intersection; and correcting the relative position between the workpiece and the thermal radiation measuring means such that the point of intersection of said visible locating beam and the desired measuring point coincide on the workpiece coating surface.

* * * * *